(12) United States Patent  
Olson et al.

(10) Patent No.: US 7,880,887 B2  
(45) Date of Patent: Feb. 1, 2011

(54) APPARATUS AND METHOD FOR MEASURING THE CONCENTRATION OF GASES IN A STERILIZATION CHAMBER

(75) Inventors: Steven J. Olson, Mahtomedi, MN (US); Jami McLaren, Crystal, MN (US); Steven K. Isvik, New Brighton, MN (US)

(73) Assignee: Phygen, Inc., Minneapolis, MN (US)

( * ) Notice: Subject to any disclaimer, the term of this patent is extended or adjusted under 35 U.S.C. 154(b) by 217 days.

(21) Appl. No.: 12/231,211

(22) Filed: Aug. 29, 2008

(65) Prior Publication Data

US 2010/0053621 A1    Mar. 4, 2010

(51) Int. Cl.  
*G01N 21/00* (2006.01)

(52) U.S. Cl. .................. 356/437; 356/432; 356/433

(58) Field of Classification Search .......... 356/432–444  
See application file for complete search history.

(56) References Cited

U.S. PATENT DOCUMENTS

| | | | |
|---|---|---|---|
| 3,972,627 A | 8/1976 | Rabl et al. | |
| 4,601,582 A | 7/1986 | Casey, Jr. | |
| 5,326,973 A | 7/1994 | Eckerbom et al. | |
| 6,184,985 B1 | 2/2001 | Chalmers et al. | |
| 6,269,680 B1 * | 8/2001 | Prieve et al. | ............... 73/23.21 |
| 7,563,329 B2 * | 7/2009 | Lin et al. | ..................... 134/18 |
| 2008/0204710 A1 | 8/2008 | Harrison et al. | |

* cited by examiner

*Primary Examiner*—Michael P Stafira  
(74) *Attorney, Agent, or Firm*—Thomas J. Nikolai; Nikolai & Mersereau, P.A.

(57) ABSTRACT

Accurate measurements of the concentration of a sterilant in a sterilization chamber are provided through the use of a light source, a first detector that receives light from the light source that has not passed through the sterilization chamber and a detector that receives light from the light source that has passed through the sterilization chamber. The light contains wavelengths known to be absorbed by the sterilant. A controller receives and processes signals received from the two detectors to cancel changes in the output of the light source and then apply a modified Beer-Lambert law to determine the concentration of the sterilant gas.

41 Claims, 7 Drawing Sheets

APPARATUS AND METHOD FOR MEASURING THE CONCENTRATION OF GASES IN A STERILIZATION CHAMBER

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Nos. W81XWH-05-1-0398 awarded by USA Medical Research ACQ Activity; N00014-06-M-0301 awarded by Office of Naval Research SBIR Phase II; and 5R44HL074653-03 awarded by National Institute of Health SBIR Phase II.

BACKGROUND OF THE INVENTION

I. Field of the Invention

This invention relates generally to the sterilization of items using a gas or vapor as a sterilant and more particularly to determining the concentration of one or more gases in a sterilization chamber.

II. Description of the Prior Art

The surfaces of virtually all objects are covered with transmissible agents such as fungi, bacteria and viruses. It is often necessary to sterilize objects such as food products, packaging, biological materials and medical implements to eliminate or make sterile such transmissible agents. Various methods for sterilizing objects have been used in the past. Known methods of sterilization include heating and chemical treatments.

Heat sterilization involves applying steam or dry heat to the objects to be sterilized for a suitable period of time. While this method of sterilization is effective for many objects, heat sterilization is not suitable for objects adversely affected by heat. Objects subjected to heat sterilization can reach 100° to 120° C., temperatures sufficiently high to cause damage to the object. Further, heat sterilization often requires large amounts of electrical power and water. These resources are not always readily available in remote locations such as a military field setting. Chemicals which have been used in the past to sterilize objects include alcohols, aldehydes, phenols, ozone, ethylene oxide, and hydrogen peroxide. Sterilization using chemicals can be accomplished at lower temperatures and can be highly effective when sterilizing heat-sensitive items. However, care must be taken to ensure all surfaces are sterilized. This is a difficult task when sterilizing catheters, tubing, and other objects with small, difficult to reach spaces. To penetrate into such spaces, chemicals in a gaseous or vaporous form have been used as sterilants.

Various gases and vapors have been used as a sterilant when sterilizing heat sensitive objects. (The words "gas" and "vapor" in their singular and plural form will be used interchangeably hereinafter to refer generically to both gases and vapors). Proper care and handling of such sterilants is crucial because of their potentially toxic nature. Using hydrogen peroxide gas as a sterilant offers certain advantages. First, it has non-toxic properties at low concentrations and therefore is not prohibitive to human handling. Second, at low concentrations hydrogen peroxide is non-corrosive and can therefore be stored for long periods of time. Even at higher concentrations suitable packaging can be employed to protect humans from exposure. When properly packaged, the shelf-life of hydrogen peroxide sterilant solutions can be multiple years in length. Third, hydrogen peroxide degrades into water and oxygen, two non-toxic byproducts. Fourth, sterilization using hydrogen peroxide gas as a sterilant can be performed at lower temperatures (55° to 60° C.) than heat sterilization. Virtually all products requiring sterilization are not adversely affected by temperatures in this range. Fifth, hydrogen peroxide gas sterilization requires less energy and essentially no water than heat sterilization.

When hydrogen peroxide gas is used as a sterilant, the concentration of hydrogen peroxide gas in a sterilization chamber must be maintained within a specific range for a predetermined time to ensure proper sterilization. The most efficient and effective hydrogen peroxide concentration range and time are dependent on the materials to be sterilized, the sterilization load and other environmental and operational factors. For this reason it is important to accurately monitor the hydrogen peroxide concentration throughout the sterilization process. The same is true for other gas sterilants.

A variety of techniques have been employed in the prior art to determine the concentration of hydrogen peroxide in a sterilization chamber. Various chemical techniques for measuring concentrations of hydrogen peroxide vapor or gas are disclosed in U.S. Pat. Nos. 6,491,881 and 6,953,549. Electrical techniques for measuring concentrations of hydrogen peroxide vapor or gas are disclosed in U.S. Pat. Nos. 6,933,733 and 6,946,852. Thermal techniques for measuring concentrations of hydrogen peroxide vapor or gas are disclosed in U.S. Pat. No. 4,843,867. All of these techniques require sophisticated calibration methods and suffer from their invasive nature.

Optical techniques have also been employed to determine the concentration of hydrogen peroxide gas and water vapor within a sterilization chamber. When such optical techniques are used, an attempt is made to measure absorption of electromagnetic radiation by the gaseous contents of the sterilization chamber and calculate concentration based upon the measured amount of absorption. Hydrogen peroxide gas is known to strongly absorb light in portions of the ultraviolet spectrum. Water vapor is known to strongly absorb light in portions of the infrared spectrum. However, these prior art techniques fail to fully account for factors that can affect the measurements taken and, thus, any calculation of concentration.

U.S. Pat. Nos. 5,600,142; 5,847,392 and 5,847,393 disclose methods which employ a spectrometer to take measurements of various wavelengths of the spectrum (e.g. 1420 nm, 915-959 nm, 1350-1400 nm, and/or 1830-2000 nm). From these readings, an effort is made to determine the concentration of water and hydrogen peroxide in the chamber. The methods disclosed in the patents are very expensive to implement with slow response times. Also, the methods described fail to account for factors other than concentration that can affect the measurements and, thus, the calculation of concentration.

U.S. Pat. No. 6,875,399 discloses a sterilization system including a sensor for detection of a component, such as hydrogen peroxide vapor, in a multi-component vapor, such as a mixture of vapor hydrogen peroxide and water supplied to a chamber of the system. The sensor preferably uses a wavelength range in which hydrogen peroxide strongly absorbs, but other components of the vapor, such as water, do not. While this avoids the need to use complex subtraction procedures normally used to remove the contribution of water or other substances from detected absorbance measurements, it fails to address other factors that can affect the measurement. For example, U.S. Pat. No. 6,875,399 discloses a probe within the sterilization chamber that can become coated with materials that affect its performance. Also, the system disclosed in the patent does not account for other factors that can affect the measurements such as changes in the output of the light source, light from other sources or other factors that can affect light absorption measurements.

U.S. Pat. No. 7,157,045 discloses a vaporizer that supplies hydrogen peroxide and water vapor to a high level disinfection or sterilization region. Light detectors detect light which has traversed a region of the treatment chamber in a first narrow portion of the spectrum which is absorbed by the hydrogen peroxide vapor, a second narrow portion of the spectrum which is absorbed by the water vapor, and a third narrow portion of the spectrum that is absorbed by neither the hydrogen peroxide vapor nor the water vapor. From these measurements, an absorbance or transmittance is measured from which the concentrations of hydrogen peroxide and water vapor are determined. The detector used to detect light in the third portion of the spectrum is intended to provide background intensity readings. Again, this system suffers from problems discussed above. Also, the light in the third portion of the spectrum can be absorbed by the parts or contents of the chamber to some degree resulting in incorrect calculations of concentration. Diagnosing problems with the chamber, its contents and the concentration measurement system itself is made more difficult by the design of the measurement system of U.S. Pat. No. 7,157,045.

U.S. Pat. No. 6,269,680 discloses an attempt to use ultraviolet light to determine the concentration of hydrogen peroxide vapor. However, the lamps disclosed for use in this patent vary in their output as they warm-up and therefore introduce the potential for creating luminosity variations that affect the measurement. Further, the lamps disclosed for use emit large amounts of heat creating a need to maintain a constant temperature in the measurement device to obtain an accurate measurement. This requirement to maintain temperature adds to the complexity and cost of the system.

In view of the foregoing, there is a real need for a non-invasive, real-time, low-cost and accurate method and apparatus for determining the concentration of a gas sterilant in a sterilization chamber. Likewise, there is a real need for such an apparatus and method that can also measure the concentration of water vapor or other gasses in the sterilization chamber. Further, there is a need for a concentration measurement system that allows for accurate evaluation and diagnosis of problems that may arise during sterilization. These needs are fully addressed by the present invention.

SUMMARY OF THE INVENTION

A first object of the present invention is to provide an apparatus capable of taking highly accurate concentration measurements of sterilant or other gases in a sterilization chamber.

A second object of the present invention is to provide such an apparatus capable of taking such measurements in real time.

A third object of the invention is to provide such an apparatus that is highly effective in measuring concentrations of hydrogen peroxide gas within the chamber.

A fourth object of the invention is to provide such an apparatus that can also accurately detect the presence of water vapor in the sterilization chamber.

A fifth object of the invention is to provide such an apparatus that can accurately measure the concentration of water vapor in the sterilization chamber A sixth object of the invention is to provide such an apparatus that can accurately and separately measure the concentration of at least two gases, for example hydrogen peroxide gas and water vapor.

A seventh object of the present invention is to provide such an apparatus that is low cost, energy efficient, highly accurate and simple to maintain.

An eighth object of the invention is to prove a system that can report and record such measurements.

A ninth object of the invention is to provide a system that can use such measurements to control the concentration of sterilant gas within the sterilization chamber.

A tenth object of the invention is to provide such an apparatus that permits the recorded measurements to be used for diagnostic purposes and quality control.

An eleventh object of the invention is to provide an apparatus that makes accurate determinations of concentration using at least one light source and at least a pair of detectors.

A twelfth object of the invention is to provide an apparatus that takes into account changes in the output of the light source(s) used that could otherwise affect the accuracy of concentration measurements.

A thirteenth object of the invention is to provide such an apparatus that takes other environmental factors into account to ensure the accuracy of measurements.

A fourteenth object of the invention is to provide an apparatus that uses such measurements of concentration to calculate and report other information germane to the sterilization process.

A fifteenth object of the present invention is to use such an apparatus to employ suitable methods for monitoring, reporting and controlling the sterilization process.

A sixteenth object of the present invention is to provide such an apparatus that can be employed virtually anywhere, even where sources of water and electrical energy are limited.

A seventeenth object of the invention is to provide an apparatus that provides diagnostic information concerning the sterilization chamber, its contents and the operation of the equipment used to measure concentration.

These and other objects are met by the present invention which can be employed virtually anywhere in the world to sterilize packaging, medical equipment and supplies and other objects. The present invention provides an apparatus and method for measuring the concentration of a sterilant gas, such as hydrogen peroxide, in a sterilization chamber. This method and apparatus is non-invasive, low cost, consumes relatively little electrical energy, takes accurate measurements in real time, and provides useful diagnostic information.

One embodiment of the apparatus includes a vessel encapsulating a sterilization chamber, a light source, a beamsplitter, first and second detectors and a controller. The vessel also will include a sealable opening used to insert items to be sterilized into and remove sterilized items from the sterilization chamber. The vessel also includes a first port for injecting a sterilant gas such as hydrogen peroxide into the chamber, a second port for supplying air to the chamber, and a third port for evacuating gases from the chamber.

The light source generates a beam of light directed toward the beamsplitter. The beamsplitter divides the beam of light into first and second portions. The first portion is directed toward and reaches the first detector without passing through the sterilization chamber. The second portion is directed through at least a portion of the sterilization chamber toward the second detector. The first and second detectors each measure the intensity of the light they receive. Proper choices of light sources and filters produce wavelengths that are known to be absorbed by the sterilant gas, but not by other materials likely to be in the beam's path. The controller receives output signals from the first detector and the second detector in real-time. The signals from the first detector and the second detector are used by the controller to calculate sterilant concentration. To improve the accuracy of this embodiment, various filters, lenses, mirrors and other such optical devices can be used to direct and control the contents of the beam travelling to the beamsplitter and the portions traveling from the beamsplitter to the detectors.

The signals provided to the controller by the first and second detectors relate to the concentration of sterilant gas (e.g. hydrogen peroxide) in the chamber. Thus, the concentration can be determined by the controller in real-time. Such concentration determinations can be reported to a user via a display or printer or stored electronically as part of a log in the memory of the controller. Likewise, the controller can use such concentration measurements to create, record and report other information relevant to the sterilization process. Examples of such information include peak concentration, integrated concentration during a predetermined time period, time averaged concentration, time above a threshold concentration, integrated concentration during the period when concentration exceeds a predetermined threshold, and rate of change in concentration. Such data can also be used for diagnostic purposes. For example, changes in concentration can be assessed to see if they fall within or outside anticipated ranges. Concentration changes falling outside of anticipated ranges could indicate conditions that negatively affect the sterilizing capability of the sterilization equipment. The controller can also use such concentration determinations to provide real time control of the sterilant concentration in the sterilization chamber. For example, the controller can provide control signals to valves or other equipment used to inject sterilant gas into the sterilization chamber or bleed the contents of the sterilization chamber.

Other embodiments of the invention provide for detection of the concentration of two gases in the sterilization chamber, e.g. hydrogen peroxide and water. These embodiments include either a light source that emits light in two distinct wavelength ranges or two separate light sources each generating light in a different range. These alternative embodiments also include three or more detectors, a controller and other optical devices to control, direct and filter the light. In one such embodiment, a beamsplitter divides the light emanating from a light source into first and second portions. The first, minor portion of the light is directed along a path that does not intersect the sterilization chamber toward the first detector. The second, major portion is directed through the sterilization chamber toward second and third detectors. This embodiment can be operated in several different modes. In one mode the third detector is not operational and the first and second detectors work as in the first embodiment to determine the concentration of a sterilant such as hydrogen peroxide. In another mode, the second detector is not operational and the first and third detectors are used to either detect or measure the concentration of another gas such as water vapor. In a third mode all three detectors are operational and measurements of the respective concentrations of both gases are made. All three modes are possible because the light source emits light and the second and third detectors detect absorption of light in two different ranges, a first range of wavelengths known to be absorbed by the first gas (but not the second gas) and a second range of wavelengths know to be absorbed by the second gas (but not the first gas). For example, when measurements of water and hydrogen peroxide are desired, the second detector is selected to detect wavelengths in the ultraviolet range known to be absorbed by hydrogen peroxide gas, but not water vapor, and the third detector is selected to detect wavelengths in the infrared range known to be absorbed by water vapor, but not hydrogen peroxide.

The various embodiments of the present invention can be employed to perform effective sterilization through real-time reporting and control of sterilant gas concentration in the sterilization chamber. This method generally includes the following steps: (a) providing a sterilization chamber having a sealable entry through which objects to be sterilized are loaded into the sterilization chamber, and a separate entry through which sterilant enters the sterilization chamber; (b) loading at least one item to be sterilized into the sterilization chamber through the sealable entry and sealing the sealable entry; (c) evacuating the pressure within the sterilization chamber to a predetermined pressure; (d) enabling a light source such that a first portion of light is directed toward a first detector without passing through the sterilization chamber and a second portion of light is directed through the sterilization chamber to a second detector; (e) introducing a sterilant into said vaporization container; and (f) using the controller to receive and process signals from the first detector and the second detector to determine the concentration of sterilant in the sterilization chamber. In the above mentioned method, the concentration level of sterilant within the sterilization chamber can be determined using either the Beer-Lambert Law:

$$I_{L,t} = I_{0,t} \exp[-\alpha(\lambda)nL]$$

or a modified version of the Beer-Lambert Law:

$$I_{L,t} = I_{L,0}\left(\frac{I_{R,t}}{I_{R,0}}\right)\exp[-\alpha(\lambda)nL].$$

The objects, attributes, advantages and novel features of the present invention will be better understood from a reading of the detailed description that follows in conjunction with the accompanying drawings.

DETAILED DESCRIPTION

The present invention relates to the sterilization of objects using a gas sterilant. To ensure proper sterilization, the concentration of the sterilant in the sterilization chamber must be maintained within a specific range for a suitable period of time. The appropriate concentration range and length of time will depend on the objects to be sterilized, the sterilization load and a variety of other factors. The present invention monitors and controls the concentration of sterilant gas over time to ensure effective and efficient sterilization.

Figure 1:
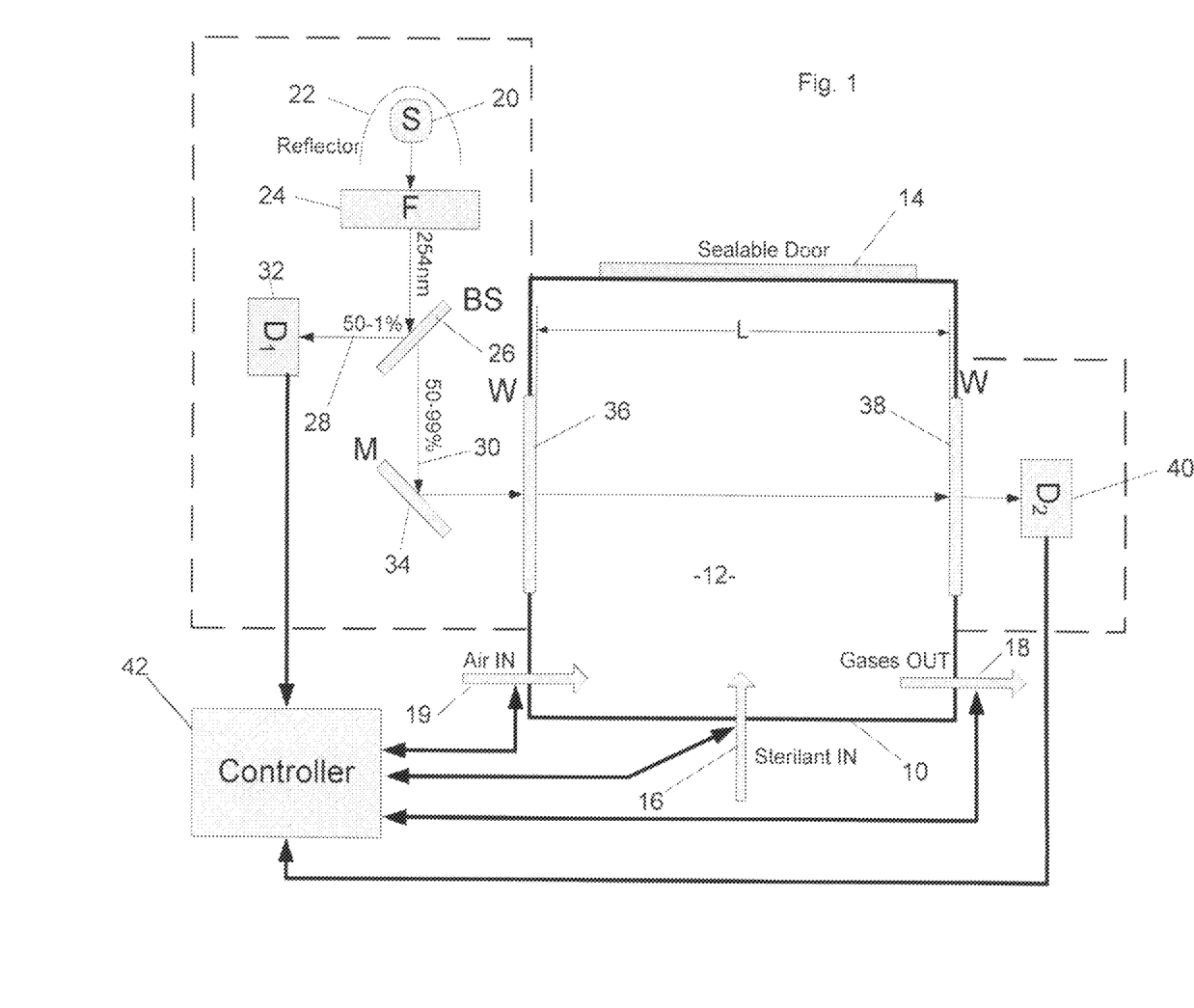
FIG. 1 is a schematic diagram of the overall system of a first preferred embodiment of the present invention.

FIG. 1 shows the present invention in its simplest form. As shown, this embodiment includes a vessel 10 surrounding a sterilization chamber 12. The vessel 10 has a sealable door 14 through which items to be sterilized can be placed into the chamber 12 and items that have been sterilized can be removed from the chamber 12. The vessel 10 also includes a port 16 through which sterilant gas can be added to the chamber 12, a port 18 through which gaseous contents of the chamber 12 can be removed from vessel 10, and a port 19 through which air can be introduced into the chamber. Typically, a valve mechanism (not shown) will be coupled to port 16 to control the addition of sterilant to the chamber. A similar valve mechanism (not shown) is coupled to port 19. Also, a valve and pump (not shown) is typically coupled to port 18 to evacuate the chamber 12.

FIG. 1 also shows the detector system of the present invention. As shown, the detector system comprises a light source 20 and a parabolic reflector 22 that collimates and directs light emitted from the light source 20 through a filter 24 and onto a beam splitter 26. Selection of the light source is based on a number of factors. Perhaps most important is that the light source generate light at wavelengths which are absorbed by the sterilant used. Likewise, the filter 24 is selected to filter out light at wavelengths other than those likely to be absorbed by the sterilant gas. The filter 24 thus serves to eliminate noise in the system that could be caused by light of other wavelengths.

The beamsplitter 26 divides the filtered light into a first minor portion 28 and a second major portion 30. As shown, the first minor portion is directed onto a first detector 32 which senses the intensity of the filtered light reaching the first detector 32. The second major portion 30 is directed onto a mirror 34 which reflects this portion of the filtered light through a first light-transmitting area such as window 36 in the wall of the vessel 10, through the sterilization chamber 12, through a second light-transmitting area such as window 38 in the opposing wall of the vessel 10 and onto a second detector 40 which senses the intensity of the filtered light reaching the second detector 40. The dotted lines in FIG. 1 represent opaque housings covering the detection system components. These housings prevent ambient light from reaching the first detector 32 and the second detector 40. The housings also protects the user from exposure to UV light.

The first detector 32 and second detector 40 each transmit signals to a controller 42. These signals represent the intensity of the light received by the detectors 32 and 40. As discussed in further detail below, these signals are compared and used by the controller to determine the concentration of sterilant gas in the chamber 12. Specifically, these signals can then be used to determine how much of the light directed at detector 42 was absorbed by sterilant in the chamber 12. The degree of absorption is a function of concentration of the sterilant. Detector 32 acts as a reference detector. Signals from detector 32 are used to detect and account for variations in the output of the lamp 20 and environmental conditions.

Figure 2:
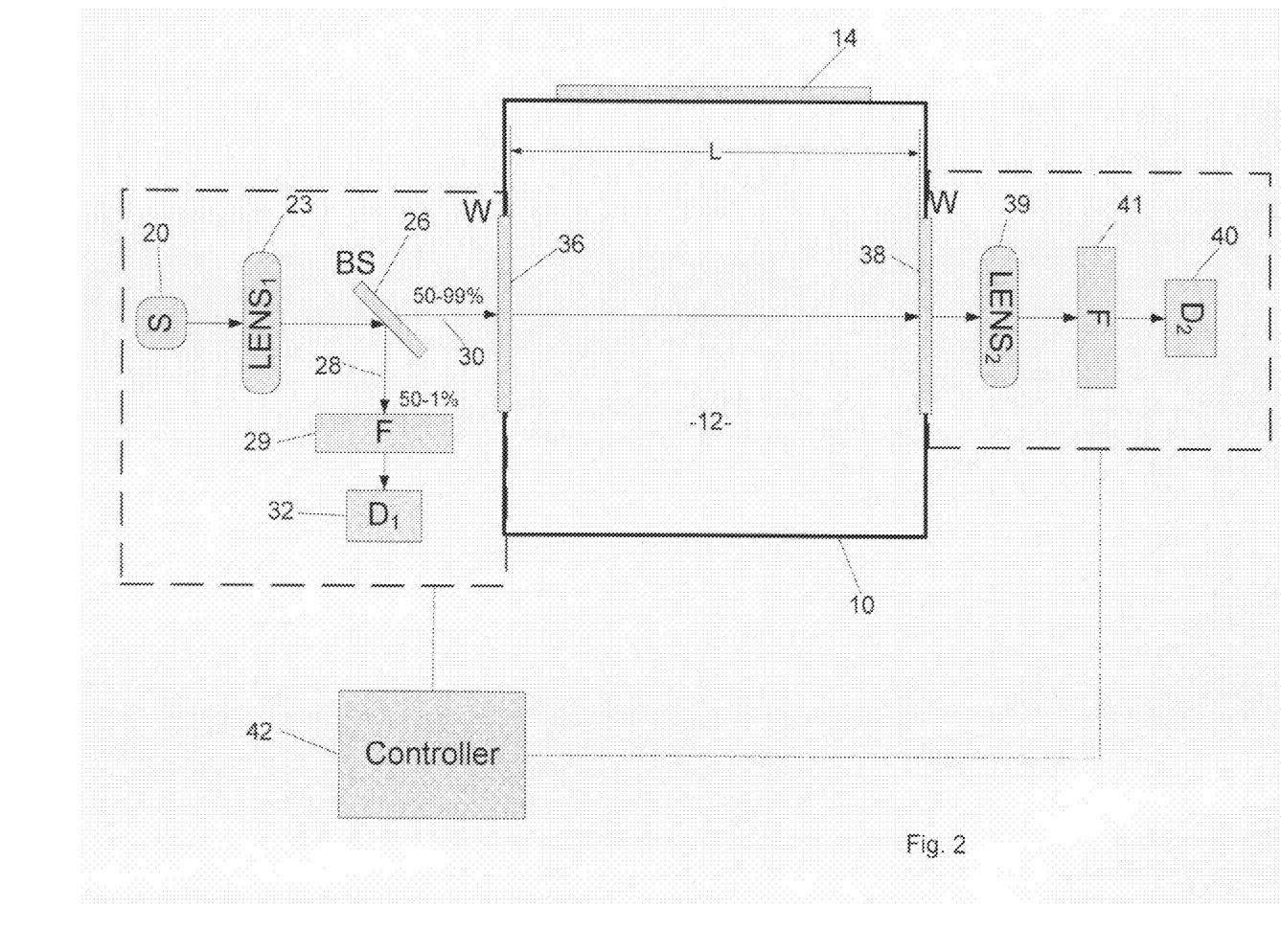
FIG. 2 is a schematic diagram of the overall system of a second embodiment of the present invention.
Figure 3:
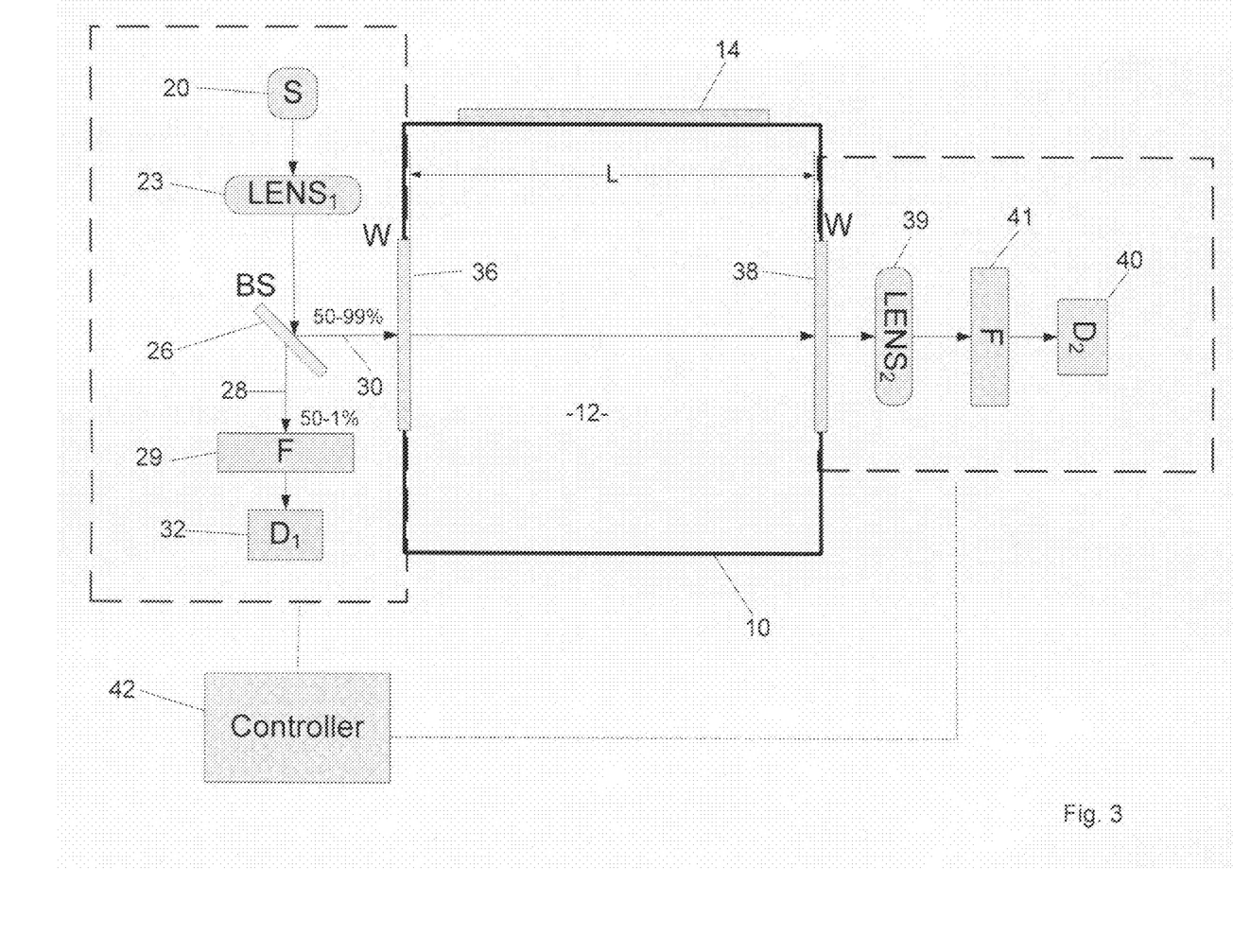
FIG. 3 is a schematic diagram of the overall system of a third embodiment of the present invention.

FIGS. 2 and 3 show similar alternative embodiments of the detection system of the present invention. In these embodiments, a light source 20 directs light through a collimating lens 23 onto the beamsplitter 26. One such example of a collimating lens includes a parabolic reflector which may be used alone or in combination with other optical lenses to improve the light collimation. The beamsplitter 26 divides the light from the light source 10 into a first minor portion 28 and a second major portion 30. The first minor portion 28 passes through a filter 29 and onto a first detector 32. The second major portion 30 passes through a first window 36, the sterilization chamber 12, a second window 38, a second collimating lens 39, a second filter 41 and onto a second detector 40. Again, the dotted lines indicate opaque housings that prevent ambient light from reaching the detectors 32 and 40. The filters 29 and 41 are preferably matched. The filters are selected to filter out wavelengths of light not typically absorbed by the sterilant to reduce noise in the system. The light source 20 is selected to provide light at wavelengths likely to be absorbed by the sterilant. The detectors 32 and 40 send signals to the controller 42 indicative of the intensity of light detected by the two detectors 32 and 40. Detector 32 acts as a reference detector accounting for variations in the output of the light source 20. The signals provided by this detector can also provide other important information regarding the operation of the system. The controller 42 then processes these signals in real time to determine the concentration of sterilant gas in the sterilization chamber.

Figure 4:
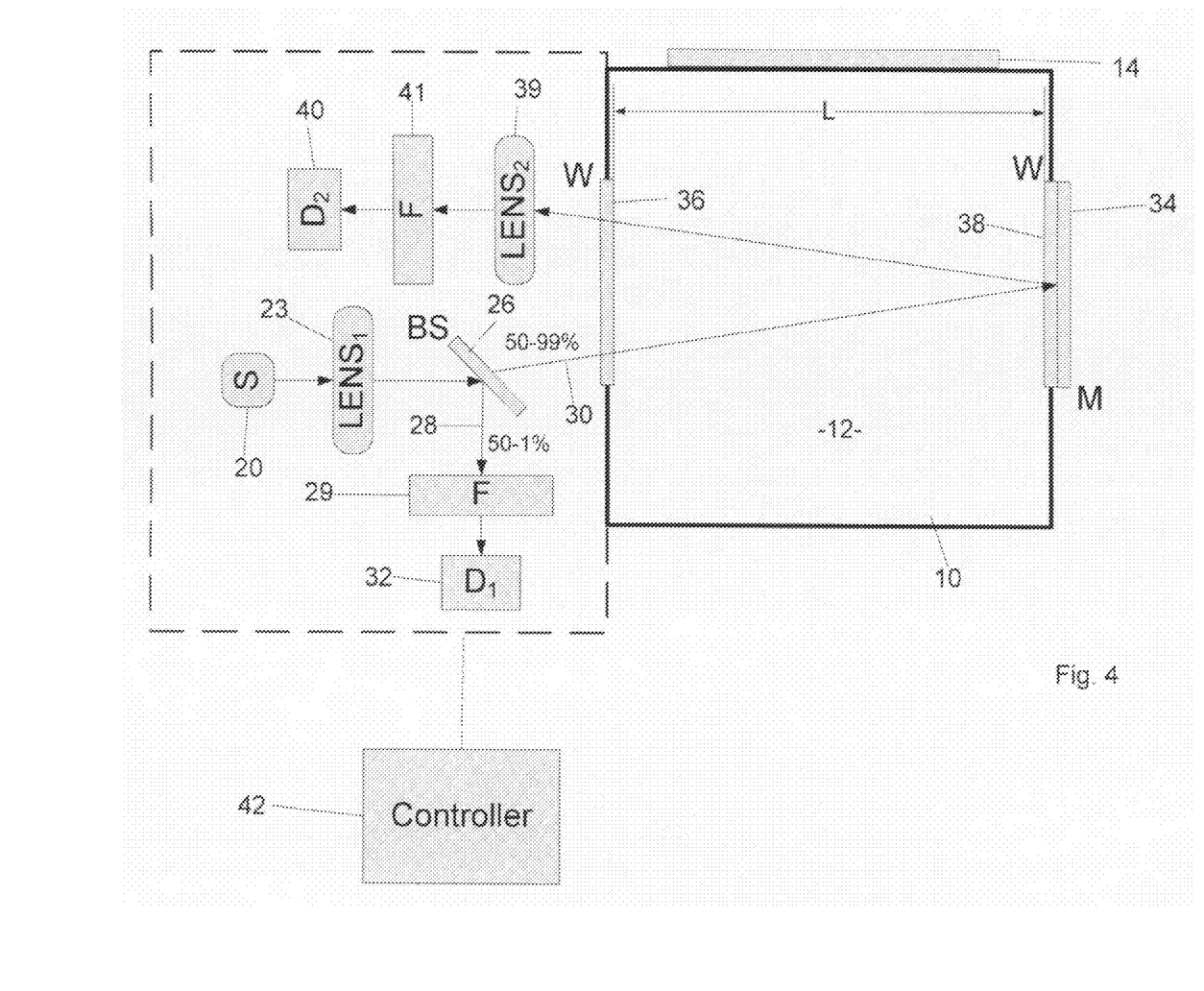
FIG. 4 is a schematic diagram of the overall system of a fourth embodiment of the present invention.

FIG. 4 shows another alternative embodiment of the present invention. In FIG. 4, the light source 20 emits light that is directed through a first collimating lens 23 to a beamsplitter 26. The beamsplitter 26 divides the light into a first minor portion 28 and a second major portion 30. The first minor portion 28 is directed through a first filter 29 and onto a reference detector 32. The second major portion 30 is directed through window 36, the sterilization chamber 12, and window 38 to a mirror 34. The mirror 34 is preferably placed in a position outside of the sterilization chamber 12 so that the mirror 34 remains free from materials which could coat the mirror and compromise the reflective qualities of the mirror. The mirror 34 then reflects the light back through this window 38, the sterilization chamber 12, and window 36. The remaining non-absorbed part of the second major portion 30 then passes through lens 39 which focuses this light through filter 41 and onto detector 40.

The embodiment shown in FIG. 4 offers several potential advantages. First, the light source 20 and the two detectors 32 and 40 can be located within a single housing. Second, wiring to the controller 42 is less cumbersome. Third, the second major portion 30 of the light passes through the sterilant in the chamber 12 twice which increases the amount of absorption that occurs. The light source 20 and filters 29 and 41 again are selected based upon the light-absorbing characteristics of the sterilant used. The light source 20 provides light in wavelengths likely to be absorbed and the filters 29 and 41 filter out light at wavelengths not absorbed by the sterilant to reduce noise in the system. Of course, the other optical components such as the windows 36 and 38, the lenses 23 and 39 and the beamsplitter 26 should be designed to allow those wavelengths absorbed by the sterilant to pass. This allows the controller 42 to accurately calculate concentration of sterilant based upon the changes in the intensity signals it receives from detectors 32 and 40 after taking into account information related to changes in the output of the light source provided by detector 32.

Figure 5:
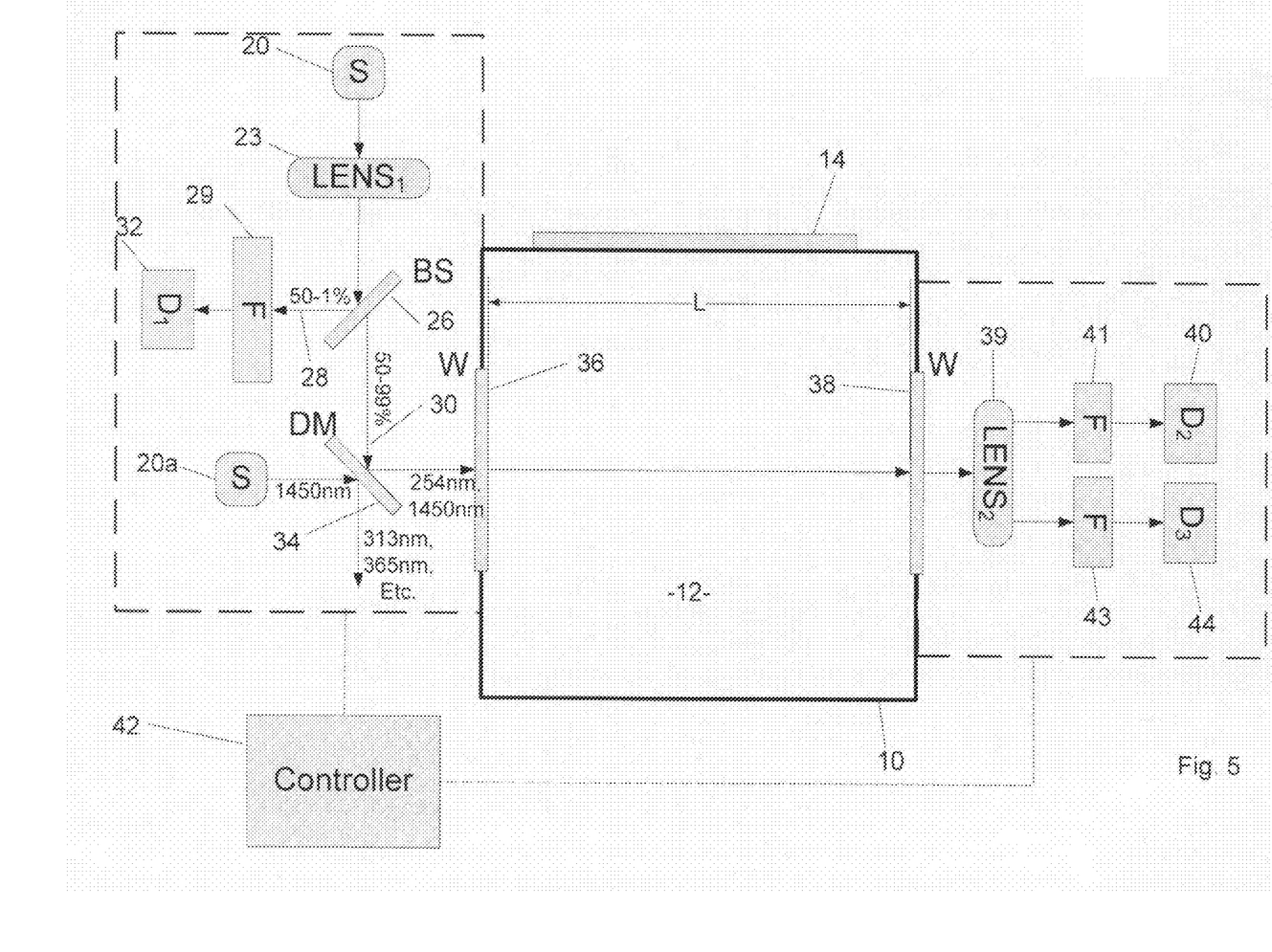
FIG. 5 is a schematic diagram of the overall system of a fifth embodiment of the present invention.

FIG. 5 shows an alternative embodiment which can be employed when it is desirable to either detect or measure the concentration of a second gas in addition to the first gas. The embodiment shown in FIG. 5 is highly effective when the two gases absorb wavelengths of light in different parts of the electromagnetic spectrum.

The embodiment shown in FIG. 5 has a pair of light sources 20 and 20a. Light source 20 emits light including a range of wavelengths known to be absorbed by the first gas, but not the second gas. Light source 20a emits light in the wavelength range known to be absorbed by the second gas, but not the first gas. Light emitted by light source 20 passes through a lens 23 to a beamsplitter 26. The beamsplitter 26 divides this light into a first minor potion 28 and a second major portion 30. The first minor portion 28 is directed through a filter 29 to a reference detector 32 without intersecting the sterilization chamber 12. This detector produces signals that vary with changes in the output of the light source 20. Since the light comprising the first minor portion 28 does not intersect the chamber 12, none of this light is absorbed by the contents of the chamber. The second major portion 30 is directed from the beamsplitter 26 to a dichroic mirror 34 which reflects this light (without substantial reduction of this light) through window 36, the sterilization chamber 12, and window 38. Light from the second light source 20a also is directed onto the dichroic mirror 34. The dichroic mirror 34 only allows light within a certain wavelength range from the second light source 20a to pass through the windows 36 and 38 and the sterilization chamber 12. The second portion of light, which is outside of the predetermined wavelength from the second light source 20a, is reflected away from the dichroic mirror 34 and may be directed to a fourth detector (not shown), or this light may be disbursed or released. The light which is emitted from the second light source 20a and passes into the sterilization chamber 12 is of a wavelength range known to be absorbed by the second gas, but not the first gas. Any of the light from either source 20 or source 20a that passes through window 38 reaches lens 39. This light is directed by lens 39 onto a pair of filters 41 and 43. Filter 41 blocks light other than light in the wavelength range absorbed by the first gas. Filter 43 blocks light other than light in the wavelength range absorbed by the second gas. Light passing through filter 41 impinges on a second detector 40. Likewise, light passing through filter 43 impinges on a third detector 44. Signals indicative of the intensity of the light reaching detectors 32, 40 and 44 are transmitted by these detectors to the controller 42.

The controller 42 receives signals from each of the first, second, third and fourth detector (if a fourth detector is implemented). The controller 42 then processes these signals to separately determine any changes in the output of the first light source 20, the second light source 20a, and light loss and absorption due to the components of the apparatus. The controller 42 of the embodiment shown in FIG. 5 also determines concentration of the first gas by comparing the intensity of the light received by detectors 32 and 40. Again, the signals from detector 32 notify the controller of variations caused by changes in the output of light source 20. Further, if the controller 42 determines that the intensity detected by detector 44 is not as high as anticipated, it assumes that the second gas is present and takes remedial measures. If one is interested in accurately measuring the concentration of the second gas, it would be a simple matter to add a second beamsplitter between the second light source 20a and the dichroic mirror 34 as well as another reference detector. Signals from this reference detector could be compared by the controller 42 to signals from the detector 44 to provide accurate real-time measurements of the concentration of a second gas and account for variations in the output of light source 20a.

The embodiment shown in FIG. 5 may have several modes of operation. For example, when sterilizing damp items it is sometimes desirable to dry the items and eliminate a second gas (e.g., water vapor) before sterilization using the first gas actually begins. This drying process may be as simple as applying a low level of heat and evacuating the chamber down to between 0 Torr and 1 Torr. During this drying process, light source 20a may be illuminated while source 20 is not. In this mode, the apparatus shown can be used to detect water vapor. If the apparatus is modified as described above, the concentration of the water vapor can be measured as well. Once the items to be sterilized and the sterilization chamber 12 are dry, it is typically no longer necessary to detect or measure water vapor. Thus, a second mode is available in which light source 20 is illuminated and light source 20a is not. In this mode, measurements of concentrations of the first sterilant gas are made, but no detection or measurement of the second gas is made. In other instances, it is desirable to separately measure the concentration of two gases during sterilization. In a third mode of operation, both light sources are illuminated and such concentration measurements taken. The filters and optics should prevent interference from the two sources operating together. If such interference is encountered, it can be easily addressed by quickly cycling between the first and second modes. This can be done so quickly that the measurements of the two gases are virtually constant.

The controller 42 can also compare expected ranges with signals received from at least one of the detectors to identify problems within the system.

Figure 6:
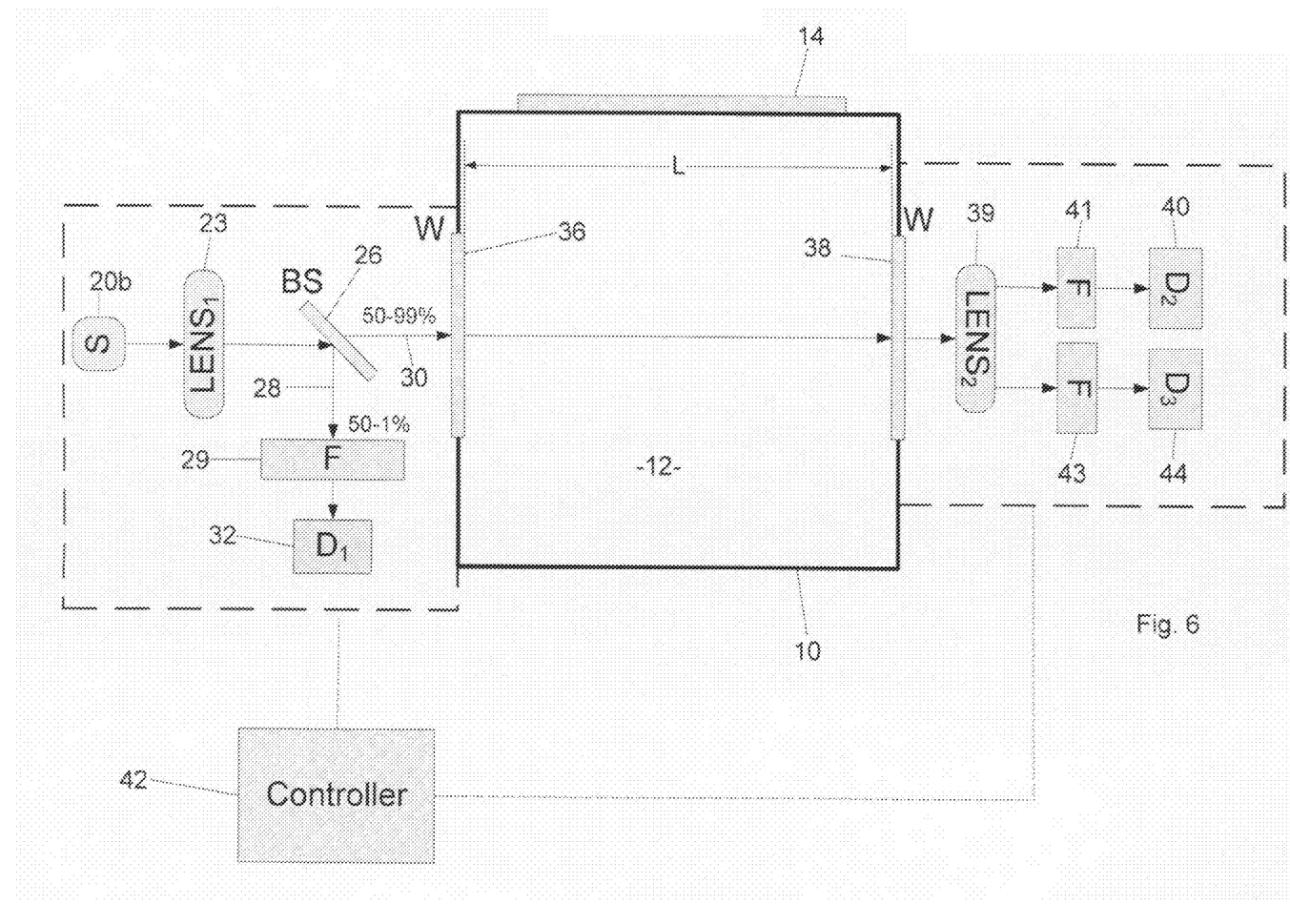
FIG. 6 is a schematic diagram of the overall system of a sixth embodiment of the present invention.

FIG. 6 discloses another embodiment that can be used to produce separate, real-time concentration measurements of two gases in the sterilization chamber. In this embodiment, a single light source 20b is used to produce light in two separate and distinct wavelength ranges. The first such range is a range known to be absorbed by the first gas, but not the other gas. The second range is a range known to be absorbed by the second gas, but not the first gas.

The light emitted by source 20b passes through a collimating optical device 23 to a beamsplitter 26. A first minor portion 28 of the light is directed through a filter 29 to a detector 32. A second major portion 30 of the light is directed by the beamsplitter 26 through window 36, the sterilization chamber 12 and window 38. Light exiting through window 38 is directed by collimating optics 39 to two filters 41 and 43. Filter 41 eliminates wavelengths of light not absorbed by the first gas and filter 43 eliminates wavelengths of light not absorbed by the second gas. Thus, light passing through filter 41 to detector 40 causes detector 40 to generate signals indicative of the absorption of light by the first gas. Likewise, the signals generated by detector 43 are indicative of the amount of absorption of light by the second gas. Since detector 32 provides signals indicative of changes in the output of the light source 20b, the signals from the three detectors 32, 40 and 44 provide the controller 42 with the information necessary not only to detect the presence of the two gases, but also to accurately measure the respective concentrations of each of the two gases.

The various embodiments described above can be successfully employed to monitor and control sterilization using hydrogen peroxide as a sterilant gas. Hydrogen peroxide absorbs light more strongly in the ultraviolet (UV) range of the electromagnetic spectrum than does water vapor which may also be found in the sterilization system. Water, on the other hand, absorbs light more strongly in portions of the infrared (IR) range of the electromagnetic spectrum.

When the embodiments of FIGS. 1-4 are employed to sterilize using hydrogen peroxide, the light source 20 is preferably a source that emits light in the UV range. Examples of such light sources include low pressure mercury vapor lamps, deuterium lamps, xenon lamps, light-emitting diodes and laser diodes. Use of a light-emitting diode (LED) is preferred because it is easier to control and more stable in intermittent use. An LED that emits light at roughly 250 nanometers (nm) is preferred because of its narrow spectral output in the range readily absorbed by hydrogen peroxide. A mercury vapor lamp also offers the advantage of providing a spectral output dominated by peak at 254 nm. This again is in the range of light wavelengths readily absorbed by hydrogen peroxide gas. Such lamps, however, have an output that varies in intensity as the lamp warms up. The reference detector 32 of each of the embodiments described above allows the system of the present invention to account for all such variations in the output of light source 20. Lens, window and detector selection are also dependent on the sterilant to be used. When hydrogen peroxide is used as a sterilant, the lenses 23 and 39 and the windows 36 and 38 of the above-described embodiments are preferably constructed from quartz or fused silica or other similar materials capable of transmitting UV light with minimal attenuation. Similarly, a beamsplitter 26 made of quartz or fused silica is preferred. Beamsplitters made of quartz are very efficient and do not absorb the light in the UV range to any significant degree. Such a beamsplitter 26 can also divide the light into a first minor portion 28 and a second major portion 30. The minor portion 28 will contain no more than half of the total light reaching the beamsplitter 26. Preferably, the first minor portion 28 will contain only about 1 to 50 percent of the light generated by light source 20. The second major portion 30, as it leaves the beamsplitter 26, will contain at least half of the light, and preferably 50 to 99 percent of the light emitted by the source 20.

The filters 24, 29 and 41 are preferably low-pass filters that permit only light of desired wavelengths to pass through the filter. For example, filters 24, 29 and 41 are preferably low-pass filters capable of filtering out all but UV light. Likewise, filter 43 is preferably a high-pass filter that permits only light in the IR range to pass. The detectors 23, 40 and 44 are each preferably a photodiode. However, other photovoltaic elements may be used. These detectors may be temperature controlled to a uniform, low temperature.

When light source 20 is illuminated, it generates UV light. This UV light is focused either by a parabolic reflector 22 (see FIG. 1) or a collimating lens 23 onto the beamsplitter 26. The first minor portion of the light (representing no more than fifty percent of the light received by the beamsplitter 26) is directed onto the detector 32 which generates a signal representative of the intensity of the light received. Either a filter 24 or a filter 29 resides between the light source 20 and the detector 32 to keep light other than UV light from reaching detector 32. The second major portion of the light reaching the beamsplitter 26 is directed through window 36, chamber 12 and window 38 onto detector 40. Again, a collimating lens 39 can be employed to focus this light onto the detector 40. If the light has not already been filtered, low-pass filter 41 can be employed to eliminate substantially all but the UV light. Again, the various elements in the path between beamsplitter 26 and detector 40 are selected because they will not significantly absorb UV light. Preferably, only the hydrogen peroxide in the chamber 12 absorbs such light to any significant degree. The detector 40 generates a signal representative of the intensity of the light it receives. The degree to which that signal will be attenuated is a function of the concentration of the UV absorbing hydrogen peroxide in the chamber.

The controller 42 which can be any suitable computer or electronic controller receives and processes the signals from the detectors 32 and 40. Any changes over time in the signal provided to controller 42 by detector 32 reflect changes in the output of light source 20. Changes over time in the signals provided by detector 40 can be a result of either changes in the output of the light source 20, such as light loss or absorption due to the components of the apparatus or changes in the concentration of hydrogen peroxide in the sterilization chamber 12. The controller can compare signals to an expected operating range to identify problems. The controller is then able to generate output signals based upon the concentration of the gas in the sterilization chamber. For example, logic in the controller 42 permits the controller to cancel out changes in the intensity of light emanating from the light source 20 and correctly calculate and report the concentration of hydrogen peroxide in the sterilization chamber 12.

When it is desirable to detect the presence of a second gas (e.g. water vapor) or measure its concentration, the embodiment of FIG. 5 can be employed. In this embodiment, measurement of the concentration of hydrogen peroxide is as described above. In this embodiment, a second light source 20a is provided. This second light source 20a emits light in the IR range, i.e. approximately 1450 nm. Such light is known to be readily absorbed by water vapor and not by hydrogen peroxide vapor. This light passes through the sterilization chamber 12 to a collimating lens 39. This light is blocked from reaching detector 40 by low pass filter 41. This light, however, passes through filter 43 to detector 44. Signals from detector 44 are compared by the controller 42 to a reference value. A signal from detector 44 less than this reference value suggests that water vapor in the chamber 12 has absorbed some of the IR light causing an attenuation of the signal from detector 44 to the controller 42. If one wants to measure the concentration of water vapor, another IR reference detector and beamsplitter are added. The signals from this additional reference detector and detector 44 are compared by the controller to cancel out changes in the output of light source 20a and calculate the concentration of water vapor.

Those skilled in the art will appreciate from the embodiment shown in FIG. 6 that a single light source and two detectors could be used to practice the present invention. For example, mercury vapor lamps with phosphor coatings are known. Such lamps not only emit UV light, but also the phosphor coating absorbs selected frequencies of light and then re-emits light in the IR region of the spectrum. Light source 20b is preferably just such a light source. When the embodiment of FIG. 6 is used in combination with a hydrogen peroxide sterilant, the beamsplitter 26 and the various lenses and windows used should not interfere with passage of either UV or IR light. The embodiment of FIG. 6 can be employed to measure the concentration of hydrogen peroxide based on absorption of the UV light and measure the concentration of water vapor based on absorption of IR light as the light passes through the chamber 12. Specifically, filter 41 can keep substantially all but UV light from reaching detector 40 and filter 43 can keep substantially all but IR light from reaching detector 44. The controller uses signals from detector 32 to identify changes in the output of light source 20b. As such, the controller can use the signals from detector 40 to calculate the concentration of hydrogen peroxide in the chamber 12 and signals from detector 44 to calculate the concentration of water vapor in the chamber 12.

The controller 42 used in any of the described embodiments can also perform a variety of tasks based upon the detection of a gas or measurement of the concentration of that gas. The controller 42 can send the concentration calculations to a display. The controller can also sound an alarm or light a warning light if an undesired gas is detected or if the concentration of desired gas is in too low. The controller can also operate a pump to evacuate the vessel 10 or take other remedial measures if an unwanted gas is present. Likewise, the controller can send control signals to valves and other equipment to control the concentration of sterilant in the chamber 12 to maintain the concentration within a desired range.

The controller can also control a printer or display to present logs, graphs and other data relevant to the sterilization process. Such logs, graphs and other data can also be stored in any storage device comprising a part of or attached to the controller 42. Such logs can be used to record various data received or calculated by the controller 42. Useful data may include peak concentrations during the sterilization cycle. Useful data may further include time-varying data such as integrated concentration during a predetermined period of time, time averaged concentration, time during which the concentration exceeded a threshold, integrated concentration during the period when concentration exceeded a predetermined threshold, rates of change in concentration, and concentration plotted with respect to time. Many other forms of data may also be created and stored.

Figure 7:
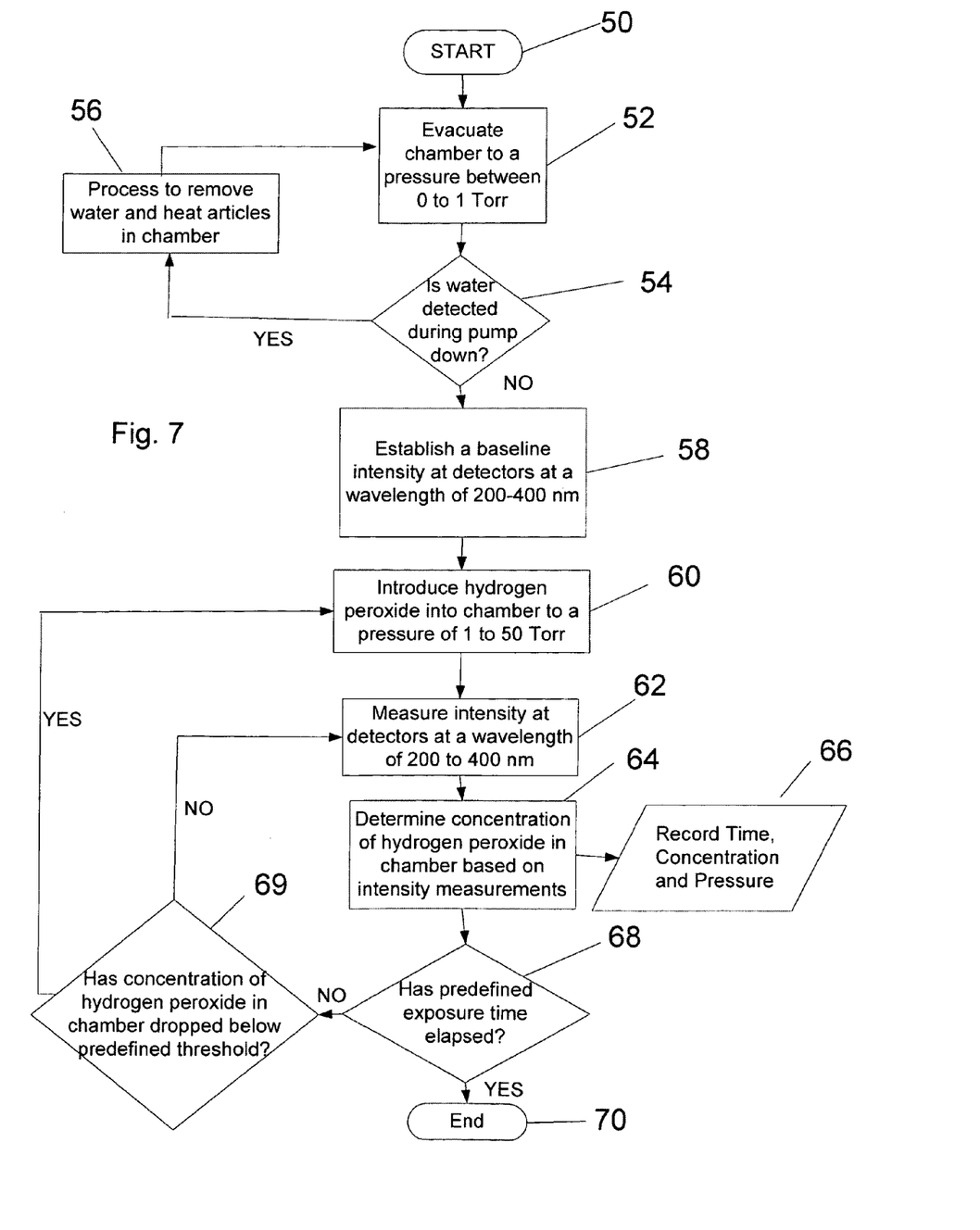
FIG. 7 is a flow chart representing a method for measuring sterilant concentration within a sterilization chamber.

FIG. 7 is a flow chart of a software routine that can be used by the controller 42 in conjunction with the apparatus of FIG. 5. Similar software routines can be employed with any of the embodiments described above. After placing one or more items to be sterilized in the sterilization chamber 12, the door or sealable entry 14 is closed and sealed and the program is started at step 50. Next, a pump is used at step 52 to evacuate the chamber 12 to a predetermined pressure. Pressures in the range of 0 to 1 Torr have been used with success. Higher pressures may be suitable as well. Once the chamber has been evacuated at step 54, light source 20a is enabled and illuminated such that a first portion of light is directed towards a first detector without passing through the sterilization chamber and a second portion of light is directed through the sterilization chamber to a second detector. The controller compares signals received from detector 44 to a predetermined threshold to determine loss and absorption of the second portion of light unrelated to absorption of light by sterilant within the chamber. This process is used to check for water vapor. If sufficiently low water vapor is detected at step 54, the process proceeds to step 58. Otherwise, the process proceeds to step 56 and a drying step occurs. The drying step may involve application of heat and further evacuation of the chamber until the signals from detector 44 fall below the predetermined threshold.

At step 58, light source 20 is illuminated. Detectors 32 and 40 provide baseline readings to the controller 42. These baseline readings indicate the intensity of light from source 20 impinging on detector 32, and more importantly, detector 40 before any hydrogen peroxide is introduced into the chamber 12. Thus, the controller can store these signals as "zero concentration" signals.

At step 60 the controller 42 opens and closes a valve at port 16 to introduce a sterilant such as hydrogen peroxide into chamber 12 until the pressure and concentration in the chamber 12 reach desired values. Successful sterilization has been achieved at pressures of 1 to 50 Torr. However, other pressures may be effective depending on the nature of the items to be sterilized and the length of time the items are subjected to the sterilization process.

At step 62, detectors 32 and 40 send signals to the controller indicative of the amount of light in the desired range impinging upon them. When hydrogen peroxide sterilization is used, light in the 200-400 nm wavelength range is typically used. This range can, of course, be increased or decreased in size depending on the optical devices employed. The signal-to-noise ratio of the system will be increased if only light of wavelengths likely to be absorbed by the sterilant is sensed by detectors 32 and 40.

At step 64, the controller 42 processes the signals received from detectors 32 and 40 to determine changes in the output of the light source and to measure the concentration of hydrogen peroxide gas in chamber 12. Such concentration measurements are periodically recorded at step 66 along with the contemporaneous total pressure in chamber 12 and the time. More specifically, when vaporized hydrogen peroxide begins entering the sterilization chamber, the detection system is used to monitor the concentration of hydrogen peroxide gas in the chamber in real-time. To do so, a controller 42 receives intensity measurements from the detectors 32 and 40 of the detection system and applies these values to the Beer-Lambert law to determine the concentration of hydrogen peroxide vapor or gas within the sterilization chamber. The controller 42 can display this information and use this information to control the concentration of hydrogen peroxide in the sterilization chamber.

The Beer-Lambert law relates absorption of light to the concentration of absorbing gas along a path in a gas layer to determine the concentration of hydrogen peroxide vapor or gas in the sterilization chamber. The Beer-Lambert Law is given by the relationship:

$$I_{L,t} = I_{0,t} \exp[-\alpha(\lambda)nL]$$

Where $I_{0,t}$ is the intensity of light entering the gas layer at time t, $I_{L,t}$ is the intensity of light leaving the gas layer at time t, $\alpha(\lambda)$ is the absorption-cross section at wavelength $\lambda$ for the absorbing species of interest (hydrogen peroxide vapor or gas, water vapor, etc.), n is the number density of hydrogen peroxide vapor or gas molecules, and L is the path length over which the absorption is taking place (or gas layer thickness), i.e. the straight line distance between light transmitting areas 20 and 22. The number density is determined as:

$$n = -\frac{\ln\left(\frac{I_{L,t}}{I_{0,t}}\right)}{\alpha(\lambda)L}$$

And the concentration follows as:

$$c = \frac{nM}{N_A}$$

where M is the molecular weight of hydrogen peroxide and $N_A$ is Avogadro's number.

For the simplifying case where the intensity of light entering the layer is constant over time:

$$I_{0,t} = I_{0,0}$$

where $I_{0,0}$ is the initial intensity at the reference detector and the further simplification that no absorbing species are present in the layer initially:

$$I_{L,0} = I_{0,0}$$

The Beer-Lambert law reduces to:

$$I_{L,t} = I_{L,0} \exp[-\alpha(\lambda)nL]$$

where, $I_{L,t}$ is the spectral emission intensity at time t, $I_{L,0}$ is the spectral emission intensity measured before vaporization of hydrogen peroxide, both measured at the detector 40 that is distant from the source. In this situation, a single detector could be used to determine concentration over time.

However, as noted above the light intensity entering the gas layer may not be constant over time due to variations in the intensity of light source 20 or other environmental conditions. In this situation, a reference detector 32 can be use to account for these variables. For example, when using a beamsplitter 26 with a first detector 32 to correct for time-varying source intensity, a modified version of the Beer-Lambert law is used:

$$I_{L,t} = I_{L,0}\left(\frac{I_{R,t}}{I_{R,0}}\right)\exp[-\alpha(\lambda)nL]$$

where $I_{R,t}$ is the intensity measured at the first (reference) detector 32 (unaffected by absorption from the environment inside the chamber), and $I_{R,0}$ is the intensity measured at the first (reference) detector 32 at the time when $I_{L,0}$ is measured at the second detector and there is negligible absorption inside the sterilization chamber 12 (such as before hydrogen peroxide is vaporized).

After the hydrogen peroxide has been vaporized, the system enters a loop in which the hydrogen peroxide vapor or gas concentration is measured at predetermined time intervals in real-time. These measurements continue until a predetermined time has elapsed. At each of the shorter time intervals, the time at which the intensity is measured and the pressure within the sterilization chamber 12 is recorded via the controller 42 or such a record can be stored electronically, printed or both. Also, at each of the shorter intervals, the hydrogen peroxide concentration within the chamber 12 is calculated and recorded via the controller 42. The concentration of water vapor within the sterilization chamber 12 could also be calculated and recorded. These calculations are performed according to the Beer-Lambert law or the modified Beer-Lambert law, as explained previously.

At step 68, the controller checks to see if a predetermined sterilization time has elapsed. If so, the sterilization process is concluded at step 70. If not, the process proceeds to step 69 and the controller 42 checks to see if the concentration has dropped below a minimum acceptable level. So long as the concentration has not dropped below the minimum acceptable level (and the predefined sterilization time has not elapsed), the program repeats steps 62-69. If the concentration drops below the minimum acceptable level, the program repeats steps 60-69. At step 60, additional hydrogen peroxide is introduced into the chamber by the controller 42 opening the valve in port 16.

As indicated above, the system of the present invention provides important diagnostic and measurement correction capabilities. For example, detector 32 is used to sense changes in the output of the light source 20. If these changes in output went undetected or were not accounted for in calculating concentration of gas in the chamber 12, errors would exist in the concentration calculations. Likewise, the controller 42 of the present invention takes baseline intensity measurements after the sterilization chamber 12 has been evacuated and before sterilant is introduced. These measurements allow the controller 42 to account for any light loss or absorption which is a function of the system components rather than the sterilant. Again, this helps ensure the accuracy of concentration measurements made by the system. The controller 42 can also store historical data and use this data to create expected operating ranges. The controller 42 can compare these expected operating ranges to data gathered during the sterilization process. If data gathered during the sterilization process falls outside of these expected ranges, a problem is reported by the controller 42. The report generated by the controller 42 provides useful information related to the nature of any problem that exists. If the problem is with the contents of the chamber, remedial measures can be taken. For example, if the windows 36 and 38 have become coated with sterilant or other materials, they can be cleaned. If the problem is with the sterilant, it can be replaced. If the problem is with the valves, pump or door, they can be repaired. If the problem is with the detection system, the modules can be quickly repaired or even replaced. This is a particularly simple task with the present invention because all of the optical devices, other than the windows, are contained in separate housings external to the chamber 12 itself and are mounted to the exterior of the vessel 10. Various replaceable modules can be provided that can be coupled to the vessel 12 and contain different light sources and filters so they are "tuned" to be used with different sterilant gases.

The foregoing description is not intended to be limiting. Instead, it has been provided to meet the disclosure requirements of the patent laws. Various changes and modifications may be made without departing from the true scope of the invention. For example, while not shown in the drawings, fiber-optic cables could be used to direct light in the system between the various optical devices. Such a fiber-optic cable could also be used to direct the light into or even though the sterilization chamber. One or more probes could likewise be employed and positioned within the sterilization chamber as a vehicle for practicing the present invention. These and other alternatives are all included within the present invention which is only limited by the claims when afforded a full range of equivalents.

What is claimed is:

1. An apparatus for measuring concentration of a gas in a sterilization chamber surrounded by a vessel comprising:
    (a) at least one light source which emits light, at least a first portion of which is directed along a path that does not intersect the sterilization chamber and a second portion of which is directed along a path that passes through at least a portion of the sterilization chamber;
    (b) a first detector which receives at least some light of the first portion;
    (c) a second detector positioned to receive at least some of the light from the second portion after the second portion has passed through the sterilization chamber; and
    (d) a controller which (i) receives signals from at least the first and second detectors, (ii) processes the signals to determine changes in the output of the said at least one light source, light loss and absorption due to components of the apparatus, and the concentration of the gas in the sterilization chamber, (iii) compares expected operating ranges with signals received from at least one of the detectors to identify problems, and (iv) generates output signals based upon the concentration of the gas in the sterilization chamber.

2. The apparatus of claim 1 further comprising at least one light transmitting area in the vessel through which the second portion may pass.

3. The apparatus of claim 1 further comprising at least one window in the vessel through which the second portion may pass.

4. The apparatus of claim 1 further comprising a third detector wherein the second detector and the third detector measure different wavelengths of light in the second portion.

5. The apparatus of claim 1 further comprising a second light source.

6. The apparatus of claim 1 further comprising a mirror.

7. The apparatus of claim 6 wherein said mirror is a dichroic mirror.

8. The apparatus of claim 1 further comprising a mirror that reflects at least some of the light of the second portion that has passed through the sterilization chamber back through the sterilization chamber to increase the light path length within the sterilization chamber.

9. The apparatus of claim 8 wherein said mirror is disposed in a position with respect to the sterilization chamber such that it remains free from materials which may compromise the reflective qualities of the mirror.

10. The apparatus of claim 1 further comprising at least one filter to limit the wavelengths of at least some of the light from the at least one light source, the first portion or the second portion to wavelengths in a desired range.

11. The apparatus of claim 10 wherein said filter is a low-pass filter.

12. The apparatus of claim 1 further comprising at least one lens to collimate at least some of the light from the at least one light source.

13. The apparatus of claim 1 further comprising a parabolic reflector to collimate light from the light source.

14. The apparatus of claim 1 further comprising at least one lens to focus at least part of one of the first or the second portions.

15. The apparatus of claim 1 further comprising at least one beamsplitter.

16. The apparatus of claim 1 further comprising at least one lens to focus at least some of the second portion exiting the sterilization chamber.

17. The apparatus of claim 1 wherein said apparatus measures the concentration of hydrogen peroxide in the sterilization chamber.

18. The apparatus of claim 1 wherein said apparatus detects the presence of water vapor in said sterilization chamber.

19. The apparatus of claim 1 wherein said apparatus measures the concentration of water vapor in said sterilization chamber.

20. The apparatus of claim 1 wherein said apparatus measures the concentration of a sterilant gas in said sterilization chamber.

21. The apparatus of claim 1 wherein said at least one light source emits light in the ultraviolet range.

22. The apparatus of claim 1 wherein said at least one light source emits light in the infrared range.

23. The apparatus of claim 20 wherein said at least one light source is a mercury vapor light source.

24. The apparatus of claim 1 wherein said controller determines the concentration of the gas in the sterilization chamber in real time.

25. An apparatus for measuring the concentration of at least two gases in a sterilization chamber surrounded by a vessel comprising:
   (a) a first light source which emits light at a first wavelength, at least a first portion of which is directed along a path that does not intersect the sterilization chamber and said second portion of which is directed along a path that passes through at least a portion of the sterilization chamber;
   (b) a second light source which emits light at a second wavelength, at least a first portion of which is directed along a path that does not intersect the sterilization chamber and said second portion of which is directed along a path that passes through at least a portion of the sterilization chamber;
   (c) a first detector which receives at least some of the light of the first portion of light from the first light source;
   (d) a second detector positioned to receive at least some of the light from the second portion of the light from the first light source;
   (e) a third detector which receives at least some of the light of the first portion of light from the second light source;
   (f) a fourth detector positioned to receive at least some of the light from the second portion of the light from the second light source;
   (g) a controller which (i) receives signals from said first, second, third and fourth detectors, (ii) processes the signals to separately determine changes in the output of the first light source and the second light source, light loss and absorption due to components of the apparatus, and the concentration of a first gas and a second gas in the sterilization chamber, (iii) compares expected operating ranges with signals received from at least one of the detectors to identify problems, and (iv) generates output signals based upon the concentration of the first gas and the second gas in the sterilization chamber.

26. A method for measuring a concentration of a gas in a sterilization chamber surrounded by a vessel comprising:
   (a) providing a sterilization chamber having a sealable entry through which objects to be sterilized are loaded into the sterilization chamber, and a separate entry through which sterilant enters the sterilization chamber;
   (b) loading at least one item to be sterilized into the sterilization chamber through the sealable entry and sealing the sealable entry;
   (c) evacuating the pressure within the sterilization chamber to a predetermined pressure;
   (d) enabling a light source such that a first portion of light is directed toward a first detector without passing through the sterilization chamber and a second portion of light is directed through the sterilization chamber to a second detector;
   (e) determining loss and absorption of the second portion of light unrelated to absorption of light by sterilant within the chamber;
   (f) introducing a sterilant into said sterilization chamber; and
   (g) using a controller to receive and process signals from said first detector and said second detector to determine changes in the output of the light source and the concentration of sterilant in the sterilization chamber, to determine whether sterilization is occurring within expected operating ranges, and to generate control signals governing the sterilization process and, if sterilization is occurring outside expected operating ranges, reporting a problem.

27. The method of claim 26 wherein said concentration of sterilant is determined in real time.

28. The method of claim 26 further comprising the step of storing said concentration in a log.

29. The method of claim 26 further comprising the step of displaying said concentration.

30. The method of claim 26 further comprising the step of storing said concentration in a data file.

31. The method of claim 26 further comprising the step of creating a data file that includes time varying data.

32. The method of claim 31 wherein said time varying data is selected at least from the following: concentration at various time intervals, integrated concentration during a predetermined time period, time averaged concentration, time above a threshold concentration, integrated concentration during the period when concentration exceeds a predetermined threshold, or rate of change in concentration.

33. The method of claim 26 further comprising the step of creating a data file that includes summary data.

34. The method of claim 33 wherein said summary data is selected at least from the following: peak concentration, integrated concentration during a predetermined time period, time averaged concentration, time above a threshold concentration, integrated concentration during the period when concentration exceeds a predetermined threshold, and rate of change in concentration.

35. The method of claim 26 further comprising the step of determining if the concentration of sterilant within the sterilization chamber is greater than or equal to a predetermined concentration level.

36. The method of claim 35 further comprising the step of adding sterilant to the sterilization chamber until the sterilant concentration reaches or exceeds a predetermined concentration level if the sterilant concentration is below said predetermined concentration level.

37. The method of claim 26 wherein sufficient sterilant is introduced into the sterilization chamber to cause the concentration of the sterilant to increase to a predetermined level.

38. The method of claim 26 wherein said sterilant is hydrogen peroxide.

39. The method of claim 26 further comprising the step of determining the presence or concentration of a second gas.

40. The method of claim 26 wherein said concentration measurements are used for diagnostic purposes.

41. The method of claim 26 wherein the concentration of gas is determined using the Beer-Lambert Law.

* * * * *